United States Patent
Bleyer et al.

(10) Patent No.: US 9,947,099 B2
(45) Date of Patent: Apr. 17, 2018

(54) REFLECTIVITY MAP ESTIMATE FROM DOT BASED STRUCTURED LIGHT SYSTEMS

(71) Applicants: Michael Bleyer, Seattle, WA (US); Raymond Kirk Price, Redmond, WA (US); Jian Zhao, Kenmore, WA (US); Denis Claude Pierre Demandolx, Bellevue, WA (US)

(72) Inventors: Michael Bleyer, Seattle, WA (US); Raymond Kirk Price, Redmond, WA (US); Jian Zhao, Kenmore, WA (US); Denis Claude Pierre Demandolx, Bellevue, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 55 days.

(21) Appl. No.: 15/221,467

(22) Filed: Jul. 27, 2016

(65) Prior Publication Data

US 2018/0033146 A1    Feb. 1, 2018

(51) Int. Cl.
*G06T 15/04* (2011.01)
*G06T 7/00* (2017.01)
*G06T 19/00* (2011.01)

(52) U.S. Cl.
CPC ............ *G06T 7/0057* (2013.01); *G06T 15/04* (2013.01); *G06T 19/006* (2013.01); *G06T 2215/16* (2013.01)

(58) Field of Classification Search
CPC .. G06T 7/0057; G06T 2215/16; G06T 19/006
See application file for complete search history.

(56) References Cited

U.S. PATENT DOCUMENTS

| | | | |
|---|---|---|---|
| 6,014,500 A | 1/2000 | Wang | |
| 8,760,499 B2 * | 6/2014 | Russell | H04N 13/0203 348/46 |
| 8,773,514 B2 | 7/2014 | Gharib et al. | |
| 8,805,057 B2 | 8/2014 | Taguchi et al. | |
| 9,007,438 B2 | 4/2015 | Mestha et al. | |
| 9,036,159 B2 | 5/2015 | Schenk | |

(Continued)

FOREIGN PATENT DOCUMENTS

WO    2016183395 A1    11/2016

OTHER PUBLICATIONS

Speiser, Stefan, "ReconstructMe selfies displayed on 3D screen", Published on: Apr. 15, 2015 Available at: http://reconstructme.net/2015/04/15/reconstructme-selfies-displayed-on-3d-screen/.
McIlroy, et al., "Kinectrack: Agile 6-DoF Tracking Using a Projected Dot Pattern", In Proceedings of IEEE International Symposium on Mixed and Augmented Reality, Nov. 5, 2012, 7 pages.
Alhwarin, et al., "IR Stereo Kinect: Improving Depth Images by Combining Structured Light with IR Stereo", In Proceedings of 13th Pacific Rim International Conference on Artificial Intelligence, Dec. 1, 2014, 9 pages.
Sarbolandi, et al., "Kinect Range Sensing: Structured-Light versus Time-of-Flight Kinect", In Journal of Computer Vision and Image Understanding, May 21, 2015, pp. 1-58.

(Continued)

*Primary Examiner* — Siamak Harandi
(74) *Attorney, Agent, or Firm* — Shook, Hardy & Bacon L.L.P.

(57) ABSTRACT

Systems and methods are provided for determining a depth map and a reflectivity map from a structured light image. The depth map can be determined by capturing the structured light image and then using a triangulation method to determine a depth map based on the dots in the captured structured light image. The reflectivity map can be determined based on the depth map and based on performing additional analysis of the dots in the captured structured light image.

20 Claims, 8 Drawing Sheets

(56) References Cited

U.S. PATENT DOCUMENTS

| | | |
|---|---|---|
| 9,098,908 B2 | 8/2015 | Kirk et al. |
| 9,148,637 B2 | 9/2015 | Anderson et al. |
| 2004/0263510 A1 | 12/2004 | Marschner et al. |
| 2010/0118123 A1 | 5/2010 | Freedman et al. |
| 2010/0177164 A1 | 7/2010 | Zalevsky et al. |
| 2013/0100256 A1* | 4/2013 | Kirk ............... G06T 7/0057 348/48 |
| 2014/0241612 A1 | 8/2014 | Rhemann et al. |
| 2014/0267611 A1 | 9/2014 | Kennett et al. |
| 2015/0003684 A1 | 1/2015 | Appia et al. |
| 2015/0062558 A1 | 3/2015 | Koppal et al. |
| 2015/0116582 A1 | 4/2015 | Yoshikawa et al. |
| 2015/0379369 A1 | 12/2015 | Liang et al. |
| 2016/0223724 A1* | 8/2016 | Hudman ............ G01B 11/2513 |
| 2016/0245920 A1* | 8/2016 | Boufounos ............ G01S 17/89 |

OTHER PUBLICATIONS

Andersen, et al., "Kinect Depth Sensor Evaluation for Computer Vision Applications", In Technical Report ECE-TR-6 of Aarhus University, Sep. 12, 2014, 39 pages.

Camplani, et al., "Efficient Spatia-Temporal Hole Filling Strategy for Kinect Depth Maps", In IS&T/SPIE Electronic Imaging, International Society for Optics and Photonics, vol. 8290, Feb. 2012, 11 Pages.

Hansard, et al., "Time of Flight Cameras: Principles, Methods and Applications", Retrieved from <https://hal.inria.fr/hal-00725654/PDF/TOF.pdf>, Nov. 2012, 103 Pages.

"International Search Report and Written Opinion Issued in PCT Application No. PCT/US2017/042952", dated Oct. 23, 2017, 18 Pages.

\* cited by examiner

REFLECTIVITY MAP ESTIMATE FROM DOT BASED STRUCTURED LIGHT SYSTEMS

BACKGROUND

One of the features of machine vision systems can be the ability to recognize a scene and identify features and objects in the scene. Having an understanding of the three-dimensional shape and object reflectivity can greatly aid in the accuracy of machine vision systems. Conventional methods for recognizing a scene can include the use of two separate types of cameras. A first camera can correspond to a structured light camera that can provide a depth map for a scene. A second camera can correspond to a conventional visible light camera that is used to determine a reflectivity map. The reflectivity map can then, for example, be used for texture mapping.

SUMMARY

In various aspects, systems and methods are provided for determining a depth map and a reflectivity map from a structured light image. The reflectivity map can correspond to reflectivity at the wavelength used by the structured light source and/or structured light camera. After projecting a structured light image onto a scene, the structured light image can be captured and processed to determine a total intensity profile for the scene that can be suitable for use, for example, as a reflectivity map. The total intensity profile can correspond to a corrected intensity profile that can reduce or minimize intensity variations that are introduced by the structured light image equipment and/or the physics of projecting and capturing a structured light image. Although the structured light image can have a density of dots projected on to the scene that is substantially lower than the number of pixels corresponding to the scene, the processing described herein can allow intensity values to be determined for pixels that are not initially associated with dots from the structured light image.

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

DETAILED DESCRIPTION

Overview

Figure 1:
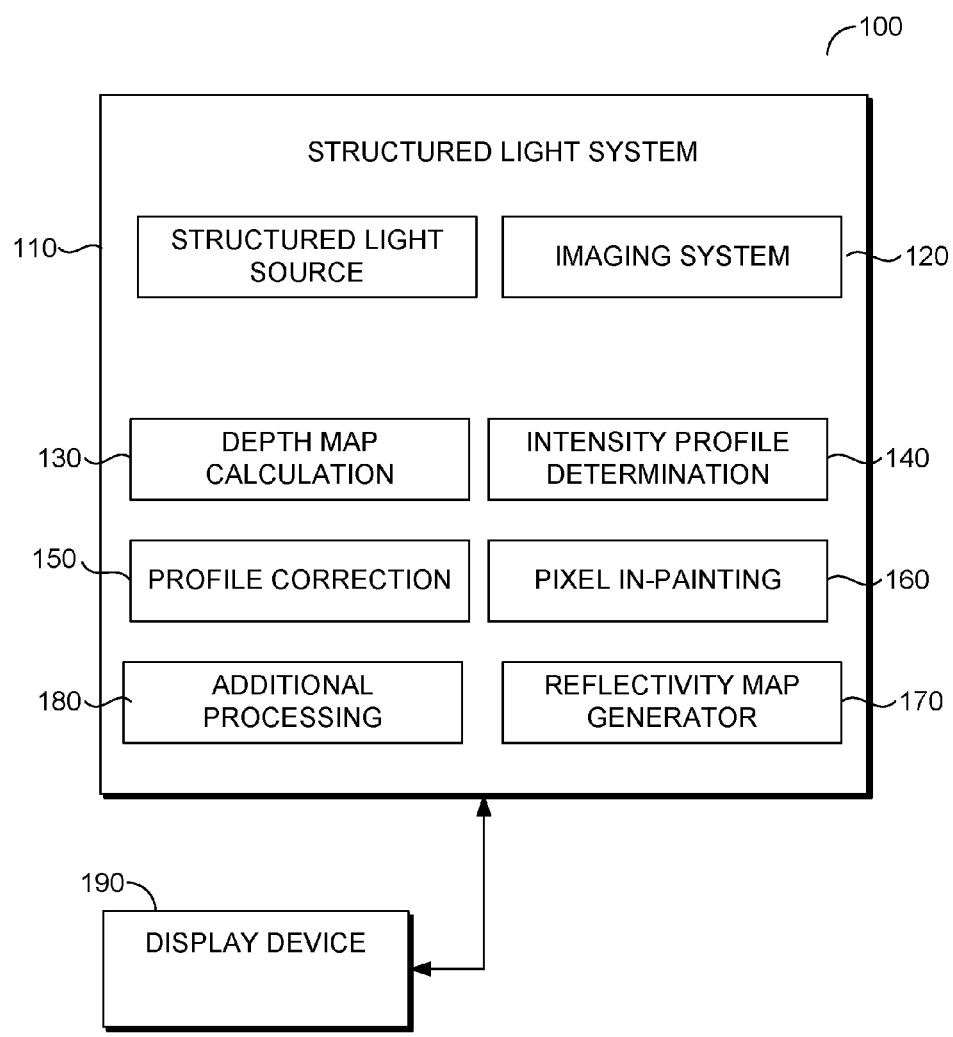
FIG. 1 schematically shows an example of a system for processing a structured light image.

In various aspects, systems and methods are provided for determining a depth map and a reflectivity map from a structured light image. The depth map and reflectivity map can be determined without requiring phase information for reflected light. The depth map can be determined by capturing the structured light image and then using a triangulation method to determine a depth profile (i.e., depth map) based on the dots in the captured structured light image. The reflectivity map can be determined based on performing additional analysis of the dots in the captured structured light image. First, dots within the structured light image can be detected. This can include determining the intensity across the size and/or shape of the dot, as opposed to simply determining or assigning a single intensity to a detected dot. The intensity for all of the detected dots can be referred to as an intensity profile. At this point, the intensity profile can correspond to a partial intensity profile, as a substantial number of pixels may not be associated with a detected dot. After detecting the dot and determining the intensity across the dot (such as for pixels associated with the dot), the intensity for the dot can be corrected. This can include, for example, correcting the intensity based on the quadratic decay due to distance, correcting for the angle of incidence of the light relative to the reflecting surface, and/or correcting for intensity losses or errors that may be associated with the illumination profile and camera imaging system. It is noted that the correction of the intensity can be based in part on information obtained from the depth map. After correction of the intensity for the detected dots, an intensity profile corresponding to the intensity corrected dots can be available. However, due to the potential presence of a substantial number of pixels not associated with a dot, the corrected intensity profile can correspond to a partial corrected intensity profile. This partial corrected intensity profile can be converted into total corrected intensity profile, potentially suitable for use as a reflectivity map, by in-painting. Based on the intensities determined for each dot, a pixel not associated with a dot can be assigned an intensity based on the intensities of detected dots in the vicinity of the pixel.

One potential application for determining a depth map and a reflectivity map using a structured light image can be for determining a mesh representation of an environment for an augmented reality device. An augmented reality device can support the presentation of augmented reality (and/or mixed-reality) images. Augmented reality images include augmented reality objects, which are virtualized objects or entities (e.g., holographic content or mixed-reality content), that are rendered for a user associated with the augmented reality device. In some aspects, free space input detected by an augmented reality device can also be used to control the device and/or interact with the environment. For example, one or more objects in an augmented reality image can be rendered based on a real world environment, where the real world environment can be captured in a digital representation by the augmented reality device. Understanding the real world environment can be based on several different techniques that provide the augmented reality device with information about the environment. This can include scanning an environment in real-time and generating a mesh representation of the environment to provide the augmented reality device with information about the environment.

If a depth map and a reflectivity map of the environment are available, the mesh representation can also be used to display an augmented reality image to a user that appears to incorporate the scanned environment. This can allow, for example, a user to navigate through a real world environment based on augmented reality objects and/or to view augmented reality objects in combination with the real world environment. Additionally or alternatively, this can allow an augmented reality device to detect user movements in the environment in order to convert the user movements into inputs for controlling the augmented reality device.

One conventional method for determining both a depth map and a reflectivity map for an environment can be to use separate cameras. A first camera (or a first plurality of cameras) can correspond to a camera, such as an infrared camera, for detecting a structured light image. The structured light image can then be used to determine a depth map for the environment. However, due in part to the sparsity of data in a structured light image, it is conventionally believed that a structured light image cannot be used to determine a reflectivity map. Instead, a second visible light camera is used to capture a visible light image (such as an RGB reflectivity image) that can be used to determine a reflectivity map for the environment. Unfortunately, typical systems involving separate cameras for capturing a structured light image and a visible light image can present difficulties due to the offset in perspective of the two separate cameras. When a depth map and a reflectivity map are generated by cameras having a different viewpoint, performing texture mapping can require warping of the reflectivity map in an attempt to convert the perspective of the reflectivity map into the perspective of the depth map. This can lead to distortions in the pixels of the reflectivity map that may be visible when displayed to a user. Additionally, due to the differing perspectives of the cameras, a portion of the pixels present in the reflectivity map may be missing in the depth map (or vice versa), which can result in an incomplete texture map.

One alternative to having separate cameras for generating a depth map and a reflectivity map can be to use time-of-flight 3D imaging. In time-of-flight 3D imaging, a scene is uniformly illuminated by a modulated signal and the sensor records the round trip time of the photons from the illuminator to the sensor. During operation, a depth map and a reflectivity map can be generated by capturing a plurality of high frequency time or phase-shifted images. By providing continuous illumination to the sensor pixels and by capturing time or phase information, a time-of-flight imaging system can allow for calculation of a depth map and a reflectivity map. However, due to the need to precisely capture time and phase information with picosecond accuracy, specialized equipment can be required for a time-of-flight system. Also, due to the nature of how the depth map is determined based on phase information in a time-of-flight 3D imaging system, multi-pass interference in images captured by the time-of-flight 3D imaging system can result in non-rigid deformations and/or distortions.

In various aspects, one or more of the above deficiencies can be overcome by determining a depth map and a reflectivity map from a captured structured light image having a sparse distribution of dots. In some aspects, the systems and methods described herein can reduce or minimize the need to time-synchronize cameras, which would be required in a setup with a physical second camera capturing a reflectivity/intensity image. In some aspects, the systems and methods described herein can allow a depth map and a reflectivity map to be determined based on an image having a single perspective, as opposed to generating a depth map and a reflectivity map based on images having different perspectives. Thus, in one or more aspects, the systems and methods described herein can provide the technical effect of improving the ability of a computing device to provide an augmented reality (and/or mixed-reality) view of an environment to a user while reducing or minimizing distortions in the view.

The reflectivity map generated from a captured structured light image can represent a reflectivity map that corresponds to a wavelength associated with a structured light system. In some aspects, a structured light source may correspond to a source that substantially emits radiation around a particular wavelength (and/or emits a single wavelength). For example, a suitable laser diode for use in a structured light source can correspond to a laser diode that substantially emits radiation at or near 850 nm. A reflectivity map generated from a structured light image generated by such a source can correspond to a reflectivity map of reflectivity at ~850 nm. In some aspects, a structured light source can provide illumination around a wavelength (or at a single wavelength) that corresponds to IR light, ultraviolet (UV) light, visible light, or another convenient wavelength that can be readily captured by an imaging device.

In this discussion, a structured light image corresponds to an image derived in part from use of a structured light source. A structured light source corresponds to a light source or illumination source that projects a plurality of dots. In some aspects, the light source for projecting a structured light image can be an infrared light source and/or another light source with reduced or minimized detectability in the visible spectrum. This can allow the structured light image to be projected on to an environment while having a reduced or minimized impact on images obtained using conventional visible light cameras (and/or other visible light detectors). The structured light image can then be captured using a corresponding camera (and/or other detector) suitable for detection of the type of light projected by the structured light source.

The dots of the structured light image can correspond to any convenient type of reference pattern, so long as the reference pattern at any point in time is known at the time of calibration (such as pre-determined). A depth map can be determined based on a structured light image by, for example, triangulation. One option for triangulation can be to have at least two cameras with overlapping fields of view for detecting the structured light image with known distance relationships between the at least two cameras. Another option can be to have a known distance relationship between the structured light source and a camera for capturing the structured light image. In this type of option, the known offset between the structured light source and the camera can be used in combination with a pre-determined reference pattern projected by the structured light source to allow the light source to be used as a "virtual camera" for purposes of triangulation.

In various aspects, the number of dots projected by a structured light source can be substantially smaller than the number of pixels used to represent an environment. As a result, the number of pixels illuminated by a dot from a structured light source can be substantially less than the total number of pixels. This can be in contrast to the light images projected by time-of-flight systems, where the projected illumination can correspond to continuous illumination or a "flood fill" that illuminates all or substantially all of the pixels in a view. For example, for structured light image based on illumination from a structured light source, the number of pixels that are (at least partially) illuminated by a dot can be 60% or less of the total number of pixels in the field of view corresponding to an environment, or 50% or less, or 25% or less, or 10% or less, or possibly even 1% or less. In some aspects, the number of pixels illuminated by a dot can be about 0.01% to about 60% of the total number of pixels in a field of view, or about 0.1% to about 60%, or about 0.01% to about 10%. Expressed as a ratio, the number of pixels illuminated by a dot versus pixels not illuminated by a dot can be 1.5 or less (i.e., 60% or less of total pixels), or 1.0 or less (i.e., 50% or less of total pixels), or 0.3 or less, or 0.1 or less. In some aspects, the ratio can be about 0.0001 to about 1.5, or about 0.001 to about 1.5, or about 0.0001 to about 0.1. Additionally or alternately, the dots projected by a structured light source can correspond to having a ratio of illuminated pixels to non-illuminated pixels, in a vertical and/or horizontal direction, of about 1.0 or less, or about 0.5 or less, or about 0.3 or less, or about 0.2 or less. In some aspects, the ratio of illuminated pixels to non-illuminated pixels, in a vertical and/or horizontal direction, can be about 0.01 to about 1.0, or about 0.05 to about 0.5, or about 0.05 to about 0.3. More generally, the dots projected by a structured light source can correspond to having a ratio of illuminated pixels to non-illuminated pixels, in a reference direction suitable for defining the nature of a structured light image of the structured light source, of about 1.0 or less, or about 0.5 or less, or about 0.3 or less, or about 0.2 or less. In this discussion, pixels that are illuminated by a dot can be referred to as pixels that cover a dot and/or that are associated with a dot.

It is noted that a ratio of illuminated to non-illuminated pixels can alternatively be converted to a ratio of illuminated pixels to total pixels. For example, a ratio of illuminated pixels to non-illuminated pixels of about 1.0 or less can correspond to a ratio of illuminated pixels to total pixels of about 0.5 or less. It is further noted that in aspects where the number of dots projected in a structured light image is substantially less than the number of pixels in a corresponding field of view, the dots projected in the structured light image may have overlap with more than one pixel.

Dot Detection

A starting point for determining a reflectivity map based on a structured light image can be related to detecting the dots in the structured light image. This can include obtaining a binary segmentation of the image such that each pixel is classified as (1) covering a dot or (2) not covering a dot. A pixel covering a dot can also be referred to as a pixel associated with a dot. This can also include determining an intensity profile based on the intensities for each detected dot. Dot detection can be performed at any convenient time, such as before, during, and/or after determining a depth profile/map for a captured structured light image. (The depth profile can be determined by any convenient method, such as triangulation.)

With regard to detecting the presence (or absence) of a dot at a pixel, a variety of strategies can be available. One option can be to perform thresholding based on a global threshold value. If the detected intensity at a pixel is greater than the global threshold value, then the pixel is considered to be associated with a dot. However, a simple threshold calculation for dot detection may perform poorly due to the varying return intensity of the dot pattern for some types of targets. For example, targets with low reflectivity, targets at larger distances from the light source, and/or targets in locations where high amounts of ambient light are present can contribute to difficulties in correctly determining whether a pixel is associated with a dot. Another option can be to perform a contrast normalization of the dot pattern before thresholding. This contrast normalization can be performed, for example, by computing the mean and standard deviation images that are obtained by calculating the average and standard deviation of intensities within small patches centered on every pixel. The mean image can then be subtracted from the original dot pattern image, and the contrast normalized image can be obtained by dividing the resulting subtracted image by the standard deviation image. Still another strategy can be to run an explicit circle detector or a local maximum detector (e.g. Laplacian) on the dot pattern image.

In addition to detecting dots and determining the pixels that are associated with a projected dot, an intensity profile can also be determined. This can include determining a plurality of intensities for each dot, such as at least one intensity for each pixel associated with a dot. Instead of sampling a single point for a dot, the intensity for a dot can be sampled/determined at multiple locations (such as sampling for each pixel and/or sampling for a plurality of locations within each pixel), so that differences in intensity across a dot can be accounted for. As an example, a dot impinging on a surface at an angle may have varying intensity across the dot due to the variation in distance across the dot. If only one sampling of the intensity of a dot is obtained, an intensity value can be assigned to the dot (and all pixels associated with the dot), but a substantial amount of intensity information can be lost.

Determining the intensity variations for the detected dots can be performed by any convenient method. The combination of the intensities for the detected dots of a structured light image can correspond to a partial intensity profile for a scene or environment associated with a structured light image.

Correction of Intensity Profile for Detected Dots

After detecting dots and determining intensities for detected dots to produce an initial partial intensity profile, the intensity profile can be corrected to determine a corrected intensity profile. In some aspects, a corrected intensity profile can be determined in part based on corrections associated with the depth map.

Structured light systems can use an active illumination source such as a laser. It is a well-known phenomenon in physics that light intensity decays with the square of distance. That means a dot at 1 meter will be 4 times as bright as a dot at 2 meters. When generating a texture map, this variation in return signal intensity with distance can be undesirable. For example, consider an attempt to generate a 3-dimensional map of a human face. As noted above, the observed dot intensity can have a quadratic dependence on distance. However, for texture mapping of the face, it can be desirable to obtain an intensity/reflectivity map that is not dependent on distance, so that any underlying differences in the reflectivity of surfaces can be detected. This type of correction to a reflectivity map to account for light decay can be performed by making use of the depth map of the structured light system. This correction factor can use the explicit depth value, as measured by the structured light response, to solve for and return the underlying value for the material reflectivity (i.e., independent of distance).

Figure 2:
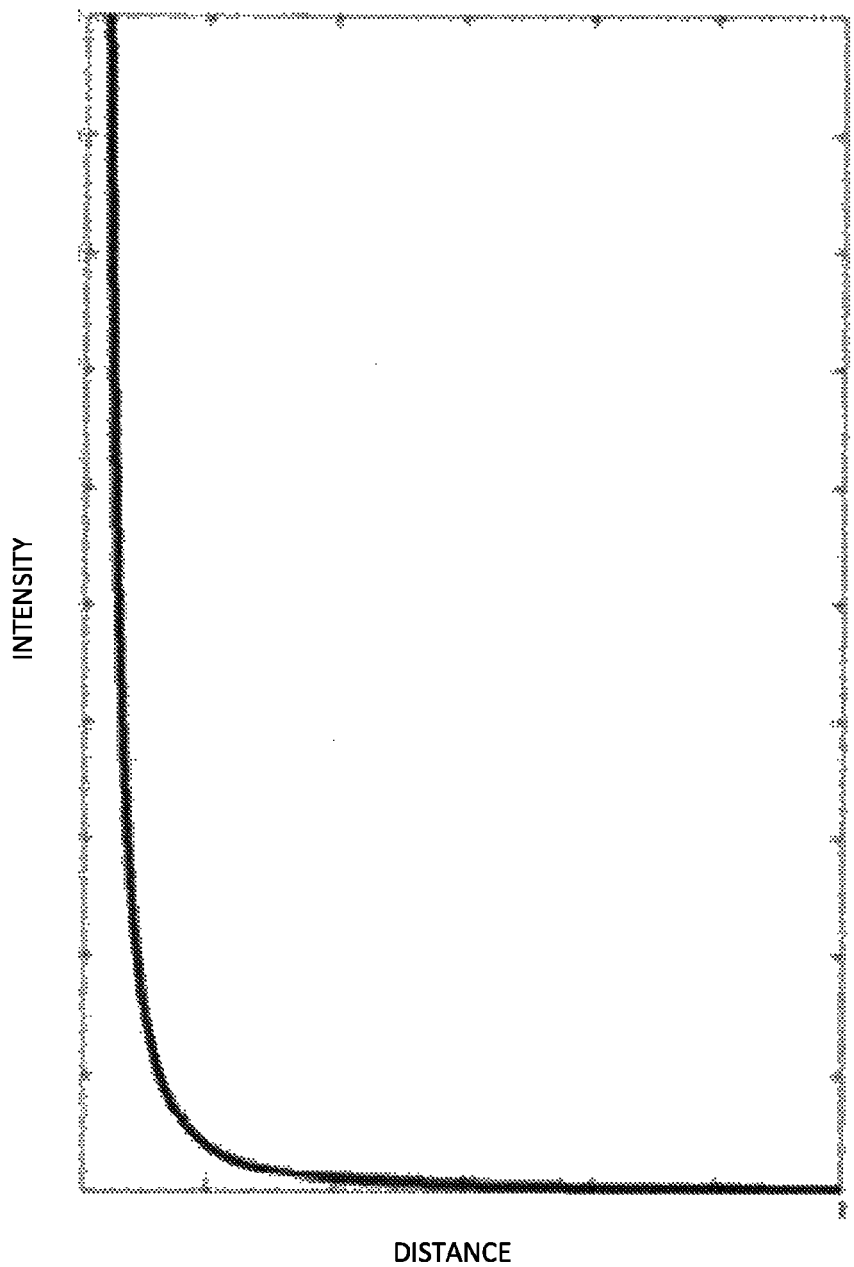
FIG. 2 shows an example of a light intensity profile as a function of distance.
Figure 3:
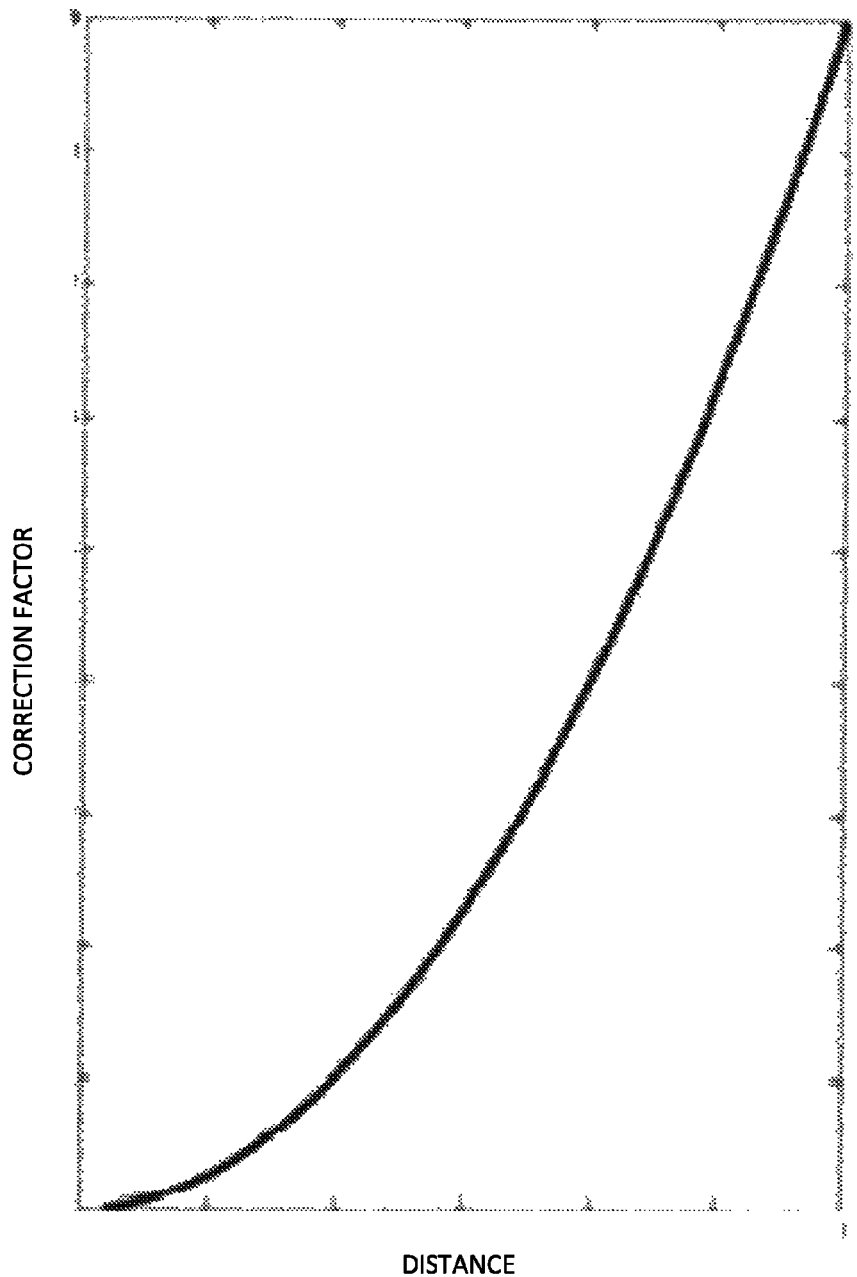
FIG. 3 shows an example of a correction factor for light intensity as a function of distance.

FIGS. 2 and 3 provide an example of how this type of distance-dependent correction can be applied. FIG. 2 shows an example of the change in intensity for reflection of a light from a surface as a function of distance. (Both the intensity and distance axes can have arbitrary units; the distance dependence curve has a similar shape for all length scales of interest herein.) In order to correct for the fall-off in intensity with distance shown in FIG. 2, a correction factor can be used, such as a correction factor sampled from a curve similar to the curve shown in FIG. 3. The units for the axes in FIG. 3 can also be arbitrary, so long as the units for the correction curve are commensurate with the units for the intensity. Multiplying the curve in FIG. 2 by the curve shown in FIG. 3 can result in a corrected intensity value that is substantially constant as a function of distance. Being able to correct intensity values to be independent of distance can allow changes in intensity/reflectivity due to other factors to be more readily identified.

In some aspects, a more sophisticated correction to a detected dot intensity can be performed by considering the angle of incidence in addition to the distance correction described above. For example, to correct a pixel p for the angle of incidence, an angle can be computed between a) the 3-dimensional ray going from the camera's focal point through pixel p and b) the normal of the surface at the location of pixel p. The reflectivity of pixel p can then be corrected by multiplying the reflectivity (before, during, or after any other corrections) with the cosine of the angle of incidence.

In some aspects, still other corrections can be applied to the detected dot intensities. Examples of additional sources of intensity error can include: variations in the illumination intensity, lens shading fall-off, and optical losses of coverglass used in the camera assembly. More generally, sources of error that can be accounted for/corrected in order to provide a corrected intensity profile for detected dots can include, but are not limited to: intensity differences due to non-uniformities in the optical element used to generate the pattern for the structured light image; intensity differences for the "zero order" dot generated by the optical element; intensity differences due to different angles of incidence; intensity differences due to different optical path lengths (i.e., distance); variations due to the cover glass for the camera detecting the intensities, which can include anti-reflection coating loss and/or angular-dependent losses; intensity loss due to the lens of the camera, including optical loss at higher angles of incidence; and/or band pass filter loss due to the presence of an IR band pass filter, including variations in loss at different angles of incidence.

After applying one or more of the above corrections intensities for detected dots, a corrected intensity profile can be available. The corrected intensity profile at this point can correspond to a corrected intensity profile for pixels associated with a detected dot in the structured light image. Due to the sparsity of dots in the structured light image, this corrected intensity profile can represent a profile for a portion of an environment or scene.

In-Painting for Calculation of Additional Portions of Intensity Profile

After determining a corrected intensity profile based on pixels associated with detected dots, an additional portion of a corrected intensity profile can be calculated so that intensity values can be assigned to pixels that are not associated with a detected dot. This type of inference of intensity values for pixels not directly associated with a detected dot can be referred to as "in-painting" of pixels. The calculation of the additional portion of the corrected intensity profile can provide a combined or total corrected intensity profile. The combined or total corrected intensity profile can comprise a sufficient density of pixels having intensity values to allow for use of the combined or total corrected intensity profile as a reflectivity map.

A variety of methods can be available for calculating intensity values for pixels that are not associated with a detected dot. Note that in this discussion, a pixel associated with a detected dot can also be referred to as a "valid" pixel, while a pixel not associated with a detected dot can be referred to as an "invalid" pixel.

As an example, one method for calculating intensity values for pixels not associated with a detected dot (i.e., invalid pixels) can include centering or otherwise constructing a window Wp around each invalid pixel p. The window Wp can be large enough so that a plurality of valid pixels are included in the interior of a constructed window. The exact window size can depend on the reference dot pattern provided by a structured light source, the camera resolution (pixel density), and/or various other factors. Depending on the aspect, the average number of valid pixels included within the windows Wp for a scene or environment can be at least 5 valid pixels, or at least 10, or at least 20, such as up to about 100 or more, and possibly up to 500 or more. For every invalid pixel p, the median reflectivity for all valid pixels within Wp can be computed. The reflectivity value of pixel p can be assigned this median reflectivity. In some aspects, the median reflectivity can be used instead of the mean or average reflectivity in order to account for situations where large variations are present in the underlying portion of the scene associated with a window, such as variations due to a discontinuity present in the underlying scene. If a few high (low) intensity pixels are present, the average value could be noticeable higher (lower) than the intensity value for the majority of pixels within the window. The median filter can enable generation of sharp discontinuities in the reflectivity map at object borders where reflectivity typically changes abruptly. Other filters such as a mean filter can instead tend to blur object boundaries. Therefore, selection of the median value can reduce or minimize difficulties with in-painting near such discontinuities in the underlying scene.

An optional refinement of the above method can be to avoid mixing reflectivities at depth discontinuities. For example, when computing the median reflectivity within Wp, valid pixels whose depth is substantially different from the depth of the center (invalid) pixel p can be excluded from the calculation of the median intensity. It has been observed that a discontinuity in the depth map can often have a corresponding discontinuity in a reflectivity map. Taking into account discontinuities in the depth map can, for example, result in better delineation of object borders. Still another option can be to compute a weighted median based on the depth map, with weights assigned based on the similarity of depth values in the depth map between a pixel p and the corresponding valid pixels within a window Wp.

Figure 4:
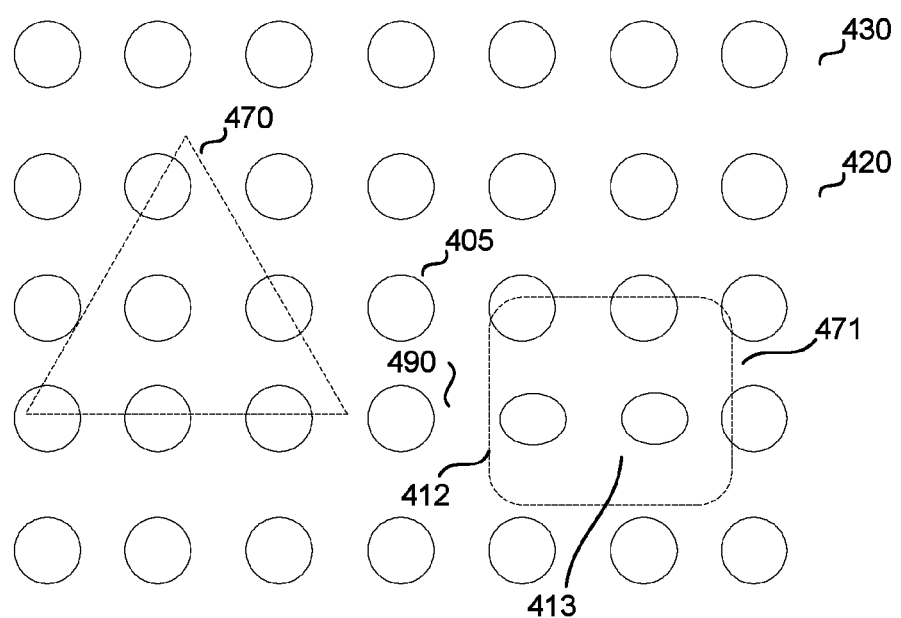
FIG. 4 schematically shows an example of a structured light image projected on a scene.
Figure 5:
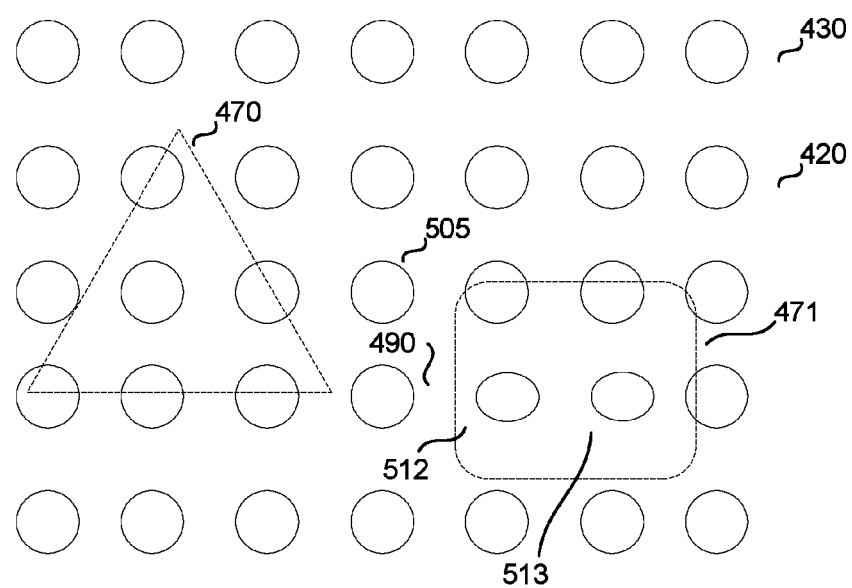
FIG. 5 schematically shows an example of a corrected intensity profile based on a structured light image.
Figure 6:
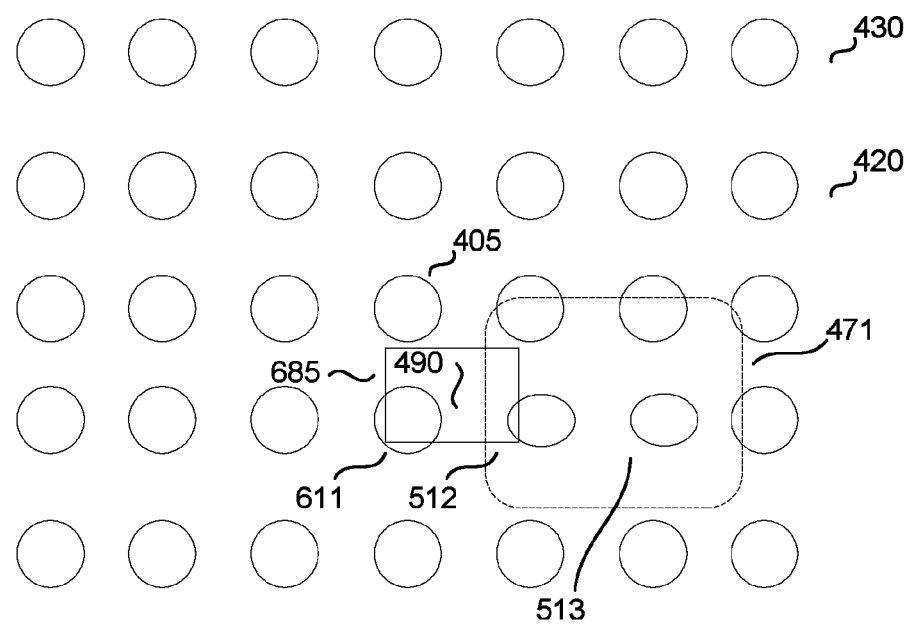
FIG. 6 schematically shows an example of calculating intensity values for pixels not associated with a dot from a structured light image.

FIGS. 4, 5, and 6 provide an example of converting a structured light image to a corrected combined or total intensity profile. FIGS. 4, 5, and 6 are schematic representations provided to facilitate explanation. For example, it is understood that the density of dots displayed in FIGS. 4 and 5 may be lower than would be expected for an actual structured light image.

FIG. 4 schematically represents a structured light image captured by a camera. The dots in the structured light image in FIG. 4 can have variations in intensity for a variety of reasons that are not directly related to the expected intensity based on the underlying scene or environment. For example, central dot 405 in FIG. 4 can have a bright than expected intensity since it is the "zero-order" diffraction dot. Also, in the hypothetical example shown in FIG. 4, due to the nature of the optical element used to generate the diffraction pattern for the dots, there is an intensity fall off for dots as the distance along the vertical axis increases. Thus, dots in rows 420 and 430 can have successively lower intensities than expected. Two objects 470 and 471 are also shown in FIG. 4 using dashed lines. The objects 470 and 471 represent objects from the underlying scene that the structured light image is being projected onto. In the hypothetical underlying scene for FIG. 4, the facing surface of object 471 is angled away from the plane of the figure. As a result, dots 412 and 413 have slightly different shape profiles than the other dots in FIG. 4. This can lead to, for example, dots 412 and 413 being associated with more pixels than the dots in other locations. In FIG. 4, element 490 indicates a pixel (or other location) that is not associated with a dot. The structured light image in FIG. 4 can be used to determine a depth map, based on knowledge of the expected reference pattern of the structured light image in comparison with the observed structured light image. It is noted that objects 470 and 471 are shown only for illustration, as such objects are not explicitly part of the structured light image and/or any subsequently determined intensity profile.

FIG. 5 represents a corrected light intensity profile that was determined based on the depth map and the structured light image shown in FIG. 4. At this stage, the corrected light intensity profile can be associated with roughly the same pixels as the pixels that were associated with dots in FIG. 4. However, the corrected light profile in FIG. 5 can be corrected to account for intensity variations due to distance and/or due to inherent properties of the structured light system. Thus, for example, the intensity of central dot 505 in FIG. 5 is corrected relative to central dot 405 in FIG. 4 to account for the additional intensity that is expected for a "zero-order" diffraction spot. Similarly, the intensities for pixels associated with dots 512 and 513 are corrected in FIG. 5 based on the corresponding depth values associated with the captured dot intensities for dots 412 and 413 in FIG. 4.

FIG. 6 shows an example of calculating an intensity for a pixel not associated with a dot. As noted in FIG. 4, pixel 490 was not initially associated with any of the dots shown in FIG. 4. A window 685 can be drawn around pixel 490. As shown in FIG. 6, window 685 includes pixels associated with a plurality of dots, including dots 611 and 512. The intensity for pixel 690 can be determined based on the median values for the valid pixels (associated with dots) within window 685. It is noted that object 471 has an object boundary between dots 611 and 512. Due to a depth map difference for the pixels associated with dots 611 and 512, the median intensity value for pixel 490 can correspond to a weighted median intensity value, with pixels associated with dot 611 receiving a higher weight due to a similar in depth values from the depth map.

Figure 8:
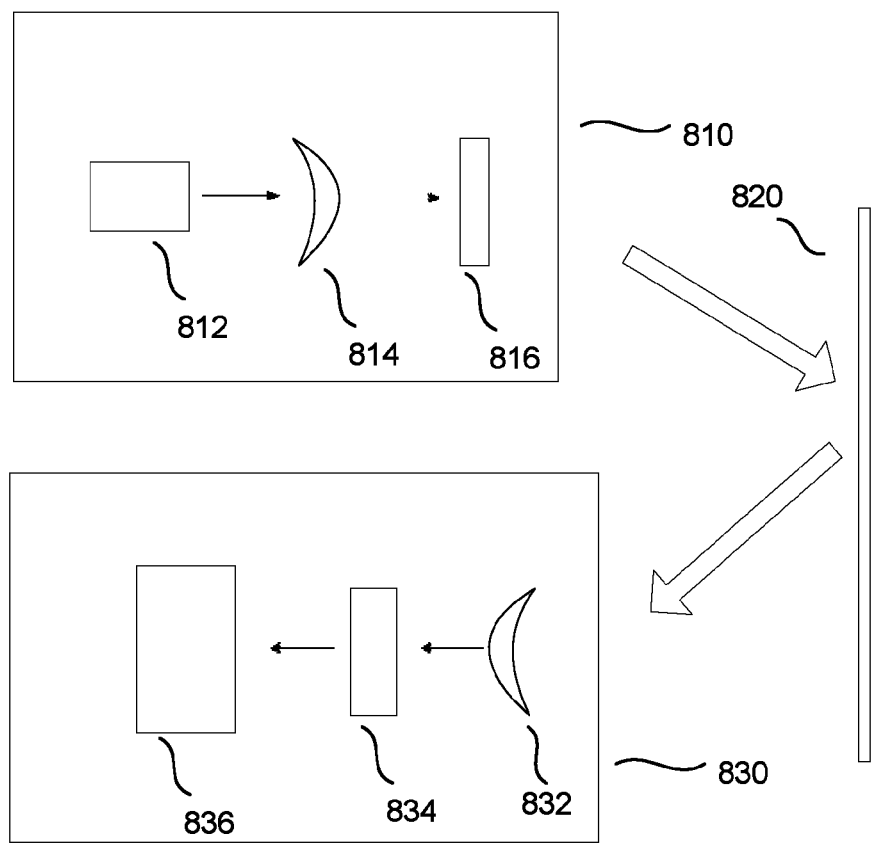
FIG. 8 schematically shows an example of structured light source and a structured light imaging system for capturing a structured light image.

FIG. 8 schematically represents a structured light source 810 and an imaging system 830 that can be used to capture a structured light image. In the example of a structured light source shown in FIG. 8, structured light source 810 includes a laser diode 812 (or optionally one or more laser diodes 812), such as a single mode laser diode, for generating light at or around a desired wavelength (or optionally wavelengths). Light from laser diode 812 can then pass through a collimating optic element 814 to provide (substantially) collimated light. The collimated light can then pass through a diffractive optic element 816 to generate light corresponding to a structured light source pattern.

The light from structured light source 810 can be used to project the structured light source pattern on to a view or scene to form a structured light image. The view or scene is schematically represented by surface 820. The structured light image can then be captured by imaging system 830. In the example shown in FIG. 8, imaging system 830 can include an imaging lens 832, one or more filters 834 (such as an IR bandpass filter), and a sensor 836.

FIG. 1 schematically represents an example of a structured light system 100 suitable for determining a reflectivity map and a depth map from a structured light image. The system shown in FIG. 1 includes a structured light source 110 for projecting a structured light image onto a scene or environment. Camera or imaging system 120 can be used to capture the projected structured light image. The captured structured light image can then be processed by one or more components in order to generate a depth map and a corrected total intensity profile that can be used as a reflectivity map. The components shown in FIG. 1 can be implemented, for example, using a processing unit with associated memory that executes computer-executable instructions. More generally, the components shown in FIG. 1 can be implemented using any convenient combination of hardware, firmware, and/or software. For convenience, a plurality of separate components are shown in FIG. 1, but it is understood that these components can be combined and/or split in any convenient manner. The components can include a depth map calculation component 130, an intensity profile determination component 140, a profile correction component 150, and an in-painting component 160. Depth map calculation component 130 can determine a depth map based on a structured light image captured by imaging system 120. Intensity profile determination component 140 can detect dots in a structured light image captured by imaging system 120, and then determine intensities for pixels associated with detected dots. Profile correction component 150 can provide a corrected intensity profile based on the determined pixel intensities from intensity profile component 140. Pixel in-painting component 160 can use the corrected intensity profile to calculate pixel intensities for pixels in additional portions of a scene that were not associated with a detected dot. Based on the pixels for additional portions of the scene generated by pixel in-painting component 160, a combined intensity profile (including the in-painted pixels) can be generated by reflectivity map generator 170 that has a sufficient number of pixels with assigned intensities to correspond to and/or allow for calculation of a reflectivity map.

Additionally, FIG. 1 shows an additional processing component for performing additional processing based on the total corrected intensity profile generated by pixel in-painting component 160 and/or the reflectivity map generated by reflectivity map generator 170. Additional processing component 180 can, for example, correspond to a texture mapping and rendering component. The output from such an additional processing component 180 could be displayed to a user via a display device 190. The display device could correspond to a conventional stand-alone video display, an augmented reality headset (i.e., a head-mounted display device), a display screen on a mobile computing device, a display screen associated with another computing device, and/or any other convenient display device.

In some aspects, the systems and/or methods described herein may be implemented in the general context of computer code or machine-useable instructions, including computer-executable instructions such as program modules, being executed by a computer or other machine, such as a personal data assistant or other handheld device. Generally, program modules including routines, programs, objects, components, data structures, etc. refer to code that perform particular tasks or implement particular abstract data types.

The invention may be practiced in a variety of system configurations, including hand-held devices, consumer electronics, general-purpose computers, more specialty computing devices, etc. The invention may also be practiced in distributed computing environments where tasks are performed by remote-processing devices that are linked through a communications network.

Computer storage media include volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device. Memory includes computer storage media in the form of volatile and/or nonvolatile memory. The memory may be removable, non-removable, or a combination thereof. Exemplary hardware devices include solid-state memory, hard drives, optical-disc drives, etc.

Computer storage media excludes signals per se. Computer storage media are in contrast to intangible computer-readable media that correspond to a modulated data signal such as a carrier wave and/or other transport mechanism. The term "modulated data signal" means a signal that has one or more of its characteristics set or changed in such a manner as to encode information in the signal. Such signals could be transported by wired media (such as a wired network or direct-wired connection) or wireless media (such as acoustic, RF, infrared and other wireless media).

Figure 7:
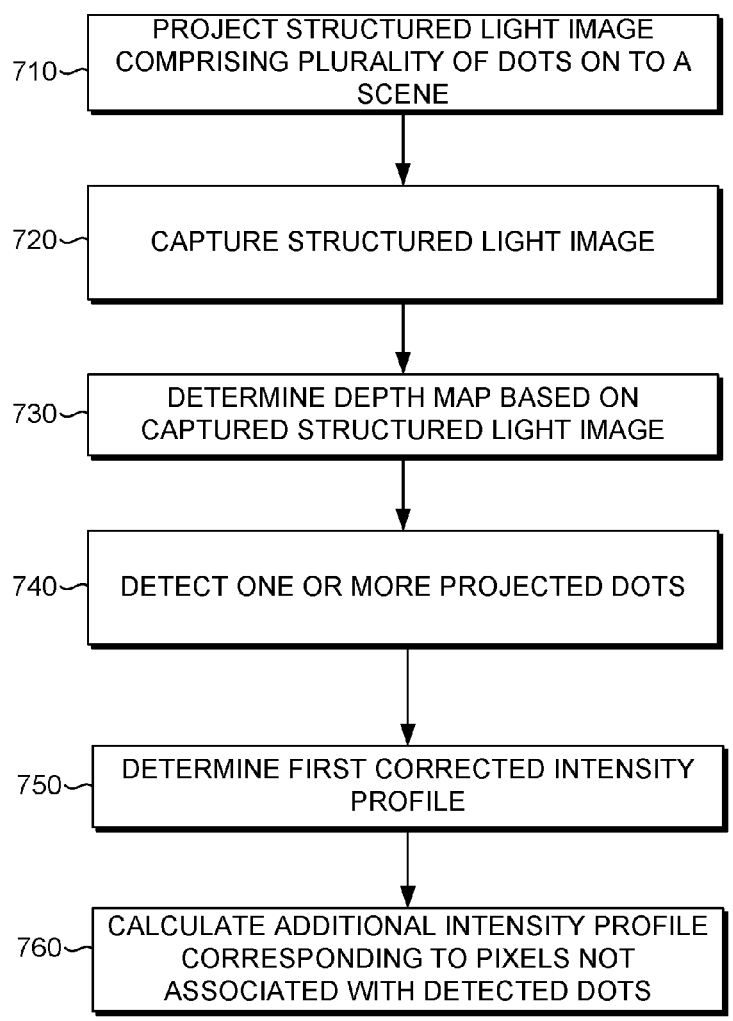
FIG. 7 shows a process flow for determining a depth map and an intensity profile from a structured light image.

FIG. 7 shows an example of a method suitable for using a structured light image to form a depth map and a reflectivity map. In the method shown in FIG. 7, a structured light image comprising a plurality of dots is projected 710 on to a scene. The structured light image can then be captured 720. Optionally, the captured structured light image can comprise a substantially greater number of pixels than dots in the structured light image. For example, a ratio of pixels associated with a dot to pixels not associated with a dot can be about 1.0 or less. A depth map can be determined 730 based on the captured structured light image. One or more of the plurality of dots can also be detected 740, such as detecting substantially all of the plurality of dots. A first corrected intensity profile can be determined 750 based on the detected dots. An additional intensity profile can then be calculated 760 based on the first corrected intensity profile. A combination of the first corrected intensity profile and the additional intensity profile can correspond to, for example, a reflectivity map.

Additional Embodiments

Embodiment 1

A method for obtaining a depth map and a reflectivity map for a scene, comprising: projecting a structured light image on to a scene, the projected structured light image comprising a plurality of dots; capturing a structured light image of a scene, the captured structured light image comprising a plurality of pixels, a ratio of pixels associated with a dot from the plurality of dots to pixels not associated with a dot from the plurality of dots being about 1.0 or less; determining a depth map based on the captured structured light image; detecting one or more of the plurality of dots projected on to the scene; determining a first corrected intensity profile, based on the determined depth map, for one or more portions of the captured structured light image corresponding to the detected dots; and calculating an additional intensity profile for at least one additional portion of the captured structured light image based on the determined first corrected intensity profile, the combined first corrected intensity profile and additional intensity profile comprising a reflectivity map.

Embodiment 2

A method for obtaining a depth map and a reflectivity map for a scene, comprising: projecting a structured light image on to a scene; capturing a structured light image of a scene, the captured structured light image comprising a plurality of pixels; determining a depth map based on the captured structured light image; detecting a plurality of dots projected on to the scene, a ratio of pixels associated with a detected dot to pixels not associated with a detected dot, in at least one of a vertical direction and a horizontal direction, being about 0.5 or less; determining a first corrected intensity profile, based on the determined depth map, for one or more portions of the captured structured light image corresponding to the detected dots; and calculating an additional intensity profile for at least one additional portion of the captured structured light image based on the determined first corrected intensity profile, the combined first corrected intensity profile and additional intensity profile comprising a reflectivity map.

Embodiment 3

The method of Embodiment 1 or 2, wherein detecting one or more of the plurality of dots projected on to the scene further comprises: identifying one or more pixels associated with each detected dot; and determining at least one intensity for the identified one or more pixels.

Embodiment 4

The method of any of the above embodiments, wherein the ratio of pixels associated with a dot from the plurality of dots to pixels not associated with a dot from the plurality of dots is about 0.1 or less; or wherein the ratio of pixels associated with a dot from the plurality of dots to pixels not associated with a dot from the plurality of dots is about 0.0001 to about 0.1.

Embodiment 5

The method of any of the above embodiments, wherein the depth map is determined by triangulation, the triangulation optionally being performed based on a) a distance between an imaging system for capturing the structured light image and a structured light source for projecting the structured light image, and b) a reference pattern for the structured light image.

Embodiment 6

The method of any of the above embodiments, wherein the corrected intensity profile comprises an intensity profile corrected based on distance, angle of incidence of the projected structured light image on a target, or a combination thereof.

Embodiment 7

The method of any of the above embodiments, wherein calculating an additional intensity profile comprises: constructing a window in the vicinity of a pixel not associated with a detected dot, an interior of the constructed window comprising a plurality of pixels associated with a detected dot; and calculating an intensity for the pixel not associated with a detected dot based on a median intensity value of the plurality of pixels associated with a detected dot in the interior of the constructed window.

Embodiment 8

The method of Embodiment 7, wherein the median intensity value comprises a weighted median intensity value, the weighting being based at least in part on the determined depth map.

Embodiment 9

The method of Embodiment 7 or 8, further comprising excluding one or more pixels associated with a detected dot in the interior of the constructed window during the calculating an intensity for the pixel not associated with a detected dot, the excluded pixels being excluded based on a difference in depth map values between the excluded pixels and the pixel not associated with a detected dot.

Embodiment 10

A system for determining a depth map and a reflectivity map, comprising: a structured light source, a structured light image projected by the structured light source comprising a plurality of dots; an imaging system for capturing the structured light image, the captured structured light image comprising a plurality of pixels, a ratio of pixels associated with a dot from the plurality of dots to pixels not associated with a dot from the plurality of dots being about 1.0 or less, the imaging system optionally comprising a camera; a depth map calculation component for determining a depth map based on the captured structured light image; an intensity profile determination component for detecting the plurality of dots and determining an intensity profile based on the detected dots; a profile correction component for determining a corrected intensity profile based on the determined intensity profile and the depth map; and a pixel in-painting component for calculating an additional intensity profile for one or more pixels not associated with a detected dot, the corrected intensity profile and the additional intensity profile comprising a reflectivity map.

Embodiment 11

The system of Embodiment 10, wherein a ratio of pixels associated with a detected dot to pixels not associated with a detected dot, in a vertical direction, a horizontal direction, or both is about 0.5 or less.

Embodiment 12

The system of Embodiment 10 or 11, wherein the profile correction component determines an intensity profile correction based on distance, angle of incidence of the projected structured light image on a target, or a combination thereof.

Embodiment 13

The system of any of Embodiments 10 to 12, wherein the structured light source comprises an optical element, the structured light image comprising a reference pattern based on the optical element.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

What is claimed is:

1. A method for obtaining a depth map and a reflectivity map for a scene, comprising:
    projecting a structured light image on to a scene, the projected structured light image comprising a plurality of dots;
    capturing a structured light image of the scene, the captured structured light image comprising a plurality of pixels, a ratio of pixels associated with a dot from the plurality of dots to pixels not associated with a dot from the plurality of dots being about 1.0 or less;
    determining a depth map based on the captured structured light image;
    detecting one or more of the plurality of dots projected on to the scene;
    determining a first corrected intensity profile, based on the determined depth map, for one or more portions of the captured structured light image corresponding to the detected dots; and
    calculating an additional intensity profile for at least one additional portion of the captured structured light image based on the determined first corrected intensity profile, the combined first corrected intensity profile and additional intensity profile comprising a reflectivity map.

2. The method of claim 1, wherein detecting one or more of the plurality of dots projected on to the scene further comprises:
    identifying one or more pixels associated with each detected dot; and
    determining at least one intensity for the identified one or more pixels.

3. The method of claim 1, wherein the ratio of pixels associated with a dot from the plurality of dots to pixels not associated with a dot from the plurality of dots is about 0.1 or less.

4. The method of claim 1, wherein the depth map is determined by triangulation.

5. The method of claim 4, wherein the triangulation is performed based on a) a distance between an imaging system for capturing the structured light image and a structured light source for projecting the structured light image, and b) a reference pattern for the structured light image.

6. The method of claim 1, wherein the corrected intensity profile comprises an intensity profile corrected based on distance.

7. The method of claim 1, wherein the corrected intensity profile comprises an intensity profile corrected based on an angle of incidence of the projected structured light image on a target.

8. The method of claim 1, wherein calculating an additional intensity profile comprises:
   constructing a window in the vicinity of a pixel not associated with a detected dot, an interior of the constructed window comprising a plurality of pixels associated with a detected dot; and
   calculating an intensity for the pixel not associated with a detected dot based on a median intensity value of the plurality of pixels associated with a detected dot in the interior of the constructed window.

9. The method of claim 8, wherein the median intensity value comprises a weighted median intensity value, the weighting being based at least in part on the determined depth map.

10. The method of claim 8, further comprising excluding one or more pixels associated with a detected dot in the interior of the constructed window during the calculating an intensity for the pixel not associated with a detected dot, the excluded pixels being excluded based on a difference in depth map values between the excluded pixels and the pixel not associated with a detected dot.

11. A system for determining a depth map and a reflectivity map, comprising:
   a structured light source, a structured light image projected by the structured light source comprising a plurality of dots;
   an imaging system for capturing the structured light image, the captured structured light image comprising a plurality of pixels, a ratio of pixels associated with a dot from the plurality of dots to pixels not associated with a dot from the plurality of dots being about 1.0 or less;
   a depth map calculation component for determining a depth map based on the captured structured light image;
   an intensity profile determination component for detecting the plurality of dots and determining an intensity profile based on the detected dots;
   a profile correction component for determining a corrected intensity profile based on the determined intensity profile and the depth map;
   a pixel in-painting component for calculating an additional intensity profile for one or more pixels not associated with a detected dot; and
   a reflectivity map generator for generating a reflectivity map based on the corrected intensity profile and the additional intensity profile.

12. The system of claim 11, wherein a ratio of pixels associated with a detected dot to pixels not associated with a detected dot, in a vertical direction, is about 0.5 or less.

13. The system of claim 11, wherein a ratio of pixels associated with a detected dot to pixels not associated with a detected dot, in a horizontal direction, is about 0.5 or less.

14. The system of claim 11, wherein the profile correction component determines an intensity profile correction based on distance.

15. The system of claim 11, wherein the profile correction component determines an intensity profile correction based on angle of incidence of the projected structured light image on a target.

16. The system of claim 11, wherein the structured light source comprises an optical element, the structured light image comprising a reference pattern based on the optical element.

17. A method for obtaining a depth map and a reflectivity map for a scene, comprising:
   projecting a structured light image on to a scene;
   capturing a structured light image of the scene, the captured structured light image comprising a plurality of pixels;
   determining a depth map based on the captured structured light image;
   detecting a plurality of dots projected on to the scene, a ratio of pixels associated with a detected dot to pixels not associated with a detected dot, in at least one of a vertical direction and a horizontal direction, being about 0.5 or less;
   determining a first corrected intensity profile, based on the determined depth map, for one or more portions of the captured structured light image corresponding to the detected dots; and
   calculating an additional intensity profile for at least one additional portion of the captured structured light image based on the determined first corrected intensity profile, the combined first corrected intensity profile and additional intensity profile comprising a reflectivity map.

18. The method of claim 17, wherein calculating an additional intensity profile comprises:
   constructing a window in the vicinity of a pixel not associated with a detected dot, an interior of the constructed window comprising a plurality of pixels associated with a detected dot; and
   calculating an intensity for the pixel not associated with a detected dot based on a median intensity value of the plurality of pixels associated with a detected dot in the interior of the constructed window.

19. The method of claim 18, wherein the median intensity value comprises a weighted median intensity value, the weighting being based at least in part on the determined depth map.

20. The method of claim 18, further comprising excluding one or more pixels associated with a detected dot in the interior of the constructed window during the calculating an intensity for the pixel not associated with a detected dot, the excluded pixels being excluded based on a difference in depth map values between the excluded pixels and the pixel not associated with a detected dot.

* * * * *